US00PP15934P2

(12) United States Plant Patent
Sakazaki

(10) Patent No.: US PP15,934 P2
(45) Date of Patent: Aug. 30, 2005

(54) *SCOPARIA* PLANT NAMED 'USSCO10'

(50) Latin Name: *Scoparia* sp.
Varietal Denomination: USSCO10

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 28 days.

(21) Appl. No.: 10/959,828

(22) Filed: Oct. 6, 2004

(51) Int. Cl.[7] ..... A01H 5/00
(52) U.S. Cl. ..... Plt./263
(58) Field of Search ..... Plt./263

(56) References Cited

PUBLICATIONS

UPOV ROM GTITM Computer Database, GTI Jouve Retrieval Software 2004/05 Citation for 'USSCO10'.*
http://www.tropilab.com/sweet–broom.html.*
http://plants.usda.gov/tmp/download144441.txt.*
http://www.rain–tree.com/vassourinha.htm.*

* cited by examiner

*Primary Examiner*—Anne Marie Grunberg
*Assistant Examiner*—W. C. Haas
(74) *Attorney, Agent, or Firm*—C. A. Whealy

(57) ABSTRACT

A new and distinct cultivar of *Scoparia* plant named 'USSCO10', characterized by its upright plant habit; freely branching growth habit; very freely flowering habit; and small light violet blue-colored flowers.

1 Drawing Sheet

Botanical designation: *Scoparia* sp.
Variety denomination: 'USSCO10'.

BACKGROUND OF THE INVENTION

The present Invention relates to a new and distinct cultivar of *Scoparia* plant, botanically known as *Scoparia* sp., and hereinafter referred to by the cultivar name USSCO10.

The new *Scoparia* is a product of a planned breeding program conducted by the Inventor in Hikone, Shiga, Japan. The objective of the breeding program is to create new freely-branching *Scoparias* with numerous flowers and attractive flower coloration.

The new *Scoparia* originated from a cross-pollination made by the Inventor on May 25, 1999 of an unnamed selection of *Scoparia* sp., not patented, as the female, or seed, parent with an unnamed *Scoparia* sp., not patented, as the male, or pollen, parent. The new *Scoparia* sp. was selected as a single plant from the resulting progeny of the cross-pollination by the Inventor on May 12, 2000 in a controlled environment in Bonsall, Calif.

Asexual reproduction of the new cultivar by terminal cuttings in a controlled environment in Bonsall, Calif. since Jul. 1, 2000, has shown that the unique features of this new *Scoparia* are stable and reproduced true to type in successive generations.

SUMMARY OF THE INVENTION

Plants of the cultivar USSCO10 have not been observed under all possible environmental conditions. The phenotype may vary somewhat with variations in environment such as temperature and light intensity without, however, any variance in genotype.

The following traits have been repeatedly observed and are determined to be the unique characteristics of 'USSCO10'. These characteristics in combination distinguish 'USSCO10' as a new and distinct cultivar of *Scoparia:*

1. Upright plant habit.
2. Freely branching growth habit.

3. Very freely flowering habit.
4. Small light violet blue-colored flowers.

Plants of the new *Scoparia* are most similar to plants of the parent selections. In side-by-side comparisons conducted in Hikone, Shiga, Japan, plants of the new *Scoparia* differed from plants of parent selections in the following characteristics:

1. Plants of the new *Scoparia* were more vigorous than plants of the parent selections.
2. Plants of the new *Scoparia* had larger flowers than plants of the parent selections.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Scoparia.*

The photograph at the top left of the sheet is a close-up view of typical flowers and leaves of 'USSCO10'.

The photograph at the top right of the sheet is a close-up of a flowering stem of 'USSCO10'.

The photograph at the bottom of the sheet comprises a side perspective view of a typical flowering plant of 'USSCO10' grown in a container.

DETAILED BOTANICAL DESCRIPTION

The aforementioned photographs and following observations and measurements describe plants grown in Bonsall, Calif. in an outdoor nursery during the late spring with day temperatures ranging from 16 to 38° C. and night temperatures ranging from 7 to 18° C. Plants were grown in 15-cm container and had been growing for about 22 weeks when the photographs and description were taken. Color references are made to The Royal Horticultural Society Colour Chart, 1995 Edition, except where general terms of ordinary dictionary significance are used.

Botanical classification: *Scoparia* sp. cultivar USSCO10.

Parentage:

*Female parent.*—Unnamed selection of *Scoparia* sp., not patented.

*Male parent.*—Unnamed selection of *Scoparia* sp., not patented.

Propagation:

*Type cutting.*—Vegetative cuttings.

*Time to initiate roots.*—About one to two weeks.

*Time to produce a rooted young plant.*—About two to three weeks.

*Root description.*—Fine; freely branching; white in color.

Plant description:

*Form.*—Upright and somewhat outwardly spreading plant habit. Freely branching growth habit with about five main branches per plant each with numerous secondary and tertiary branches. Moderately vigorous growth habit.

*Plant height.*—About 43 cm.

*Plant diameter.*—About 42 cm.

*Lateral branches.*—Length: About 30 cm. Diameter: About 5 mm. Internode length: About 2 cm. Strength: Strong. Texture: Smooth, glabrous. Color, young stems: 144A. Color, older stems: 177B.

*Foliage description.*—Arrangement: Whorled; simple; sessile. Length: About 1.2 cm. Width: About 1 mm. Shape: Narrow; linear. Apex: Acute. Base: Attenuate. Margin: Entire. Texture, upper and lower surfaces: Smooth, glabrous. Venation pattern: Parallel. Color: Developing and fully expanded foliage, upper surface: 147A. Developing and fully expanded foliage, lower surface: 147A. Venation, upper and lower surfaces: 147A.

Flower description:

*Flower type and habit.*—Solitary axillary rounded flowers; typically three per node. Flowers not persistent. Flowers face mostly outwardly.

*Quantity.*—Very freely flowering; more than 100 flowers per lateral branch.

*Natural flowering season.*—Plants flower year round in Southern California; flowering continuous during this period. Plants start flowering about four weeks after planting.

*Flower longevity on the plant.*—About four to five days.

*Fragrance.*—Not detected.

*Flower size.*—Length: About 1 cm. Width: About 1 cm. Depth: About 6 mm.

*Flower buds.*—Length: About 4 mm. Diameter: About 2 mm. Shape: Ovoid. Color: 97A.

*Petals.*—Quantity/arrangement: Four petals in a single whorl. Length: About 6 mm. Width: About 5 mm. Shape: Obovate. Apex: Rounded. Margin: Entire. Texture, upper and lower surfaces: Smooth, satiny. Color: When opening, upper surface: 97A. When opening, lower surface: 97B. Fully opened, upper surface: 97A; towards the base, 97B. Fully opened, upper surface: 97B; towards the base, 97D.

*Sepals.*—Arrangement/appearance: Single whorl of five sepals; fused at the base. Length: About 2 cm. Width: About 1.5 mm. Shape: Elliptic. Apex: Acute. Base: Fused. Margin: Entire. Texture, upper and lower surfaces: Smooth, glabrous. Color, upper and lower surfaces: 144C.

*Peduncles.*—Length: About 8 mm. Width: Less than 1 mm. Angle: About 45° from stem axis. Strength: Strong. Texture: Smooth, glabrous. Color: 144A.

*Reproductive organs.*—Stamens: Quantity per flower: Four. Anther shape: Rounded. Anther length: Less than 1 mm. Anther color: 158B. Pollen amount: Scarce. Pollen color: 162A. Pistils: Quantity per flower: One. Pistil length: About 5 cm. Style length: About 2.5 mm. Style color: 92C. Stigma shape: Rounded. Stigma color: 92A. Ovary color: 145C.

*Fruit/seed.*—Fruit and seed production has not been observed.

Disease/pest resistance: Plants of the new *Scoparia* have not been noted to be resistant to pathogens or pests common to *Scoparia.*

Temperature tolerance: Plants of the new *Scoparia* have been observed to tolerate temperatures from 0 to 43° C.

It is claimed:

1. A new and distinct cultivar of *Scoparia* plant named 'USSCO10', as illustrated and described.

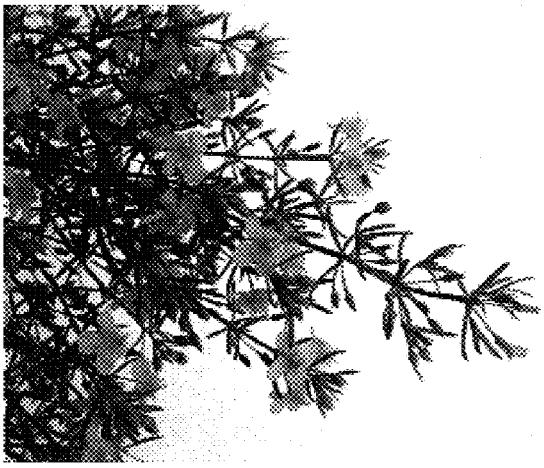
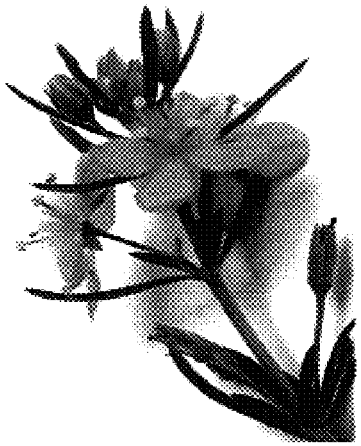
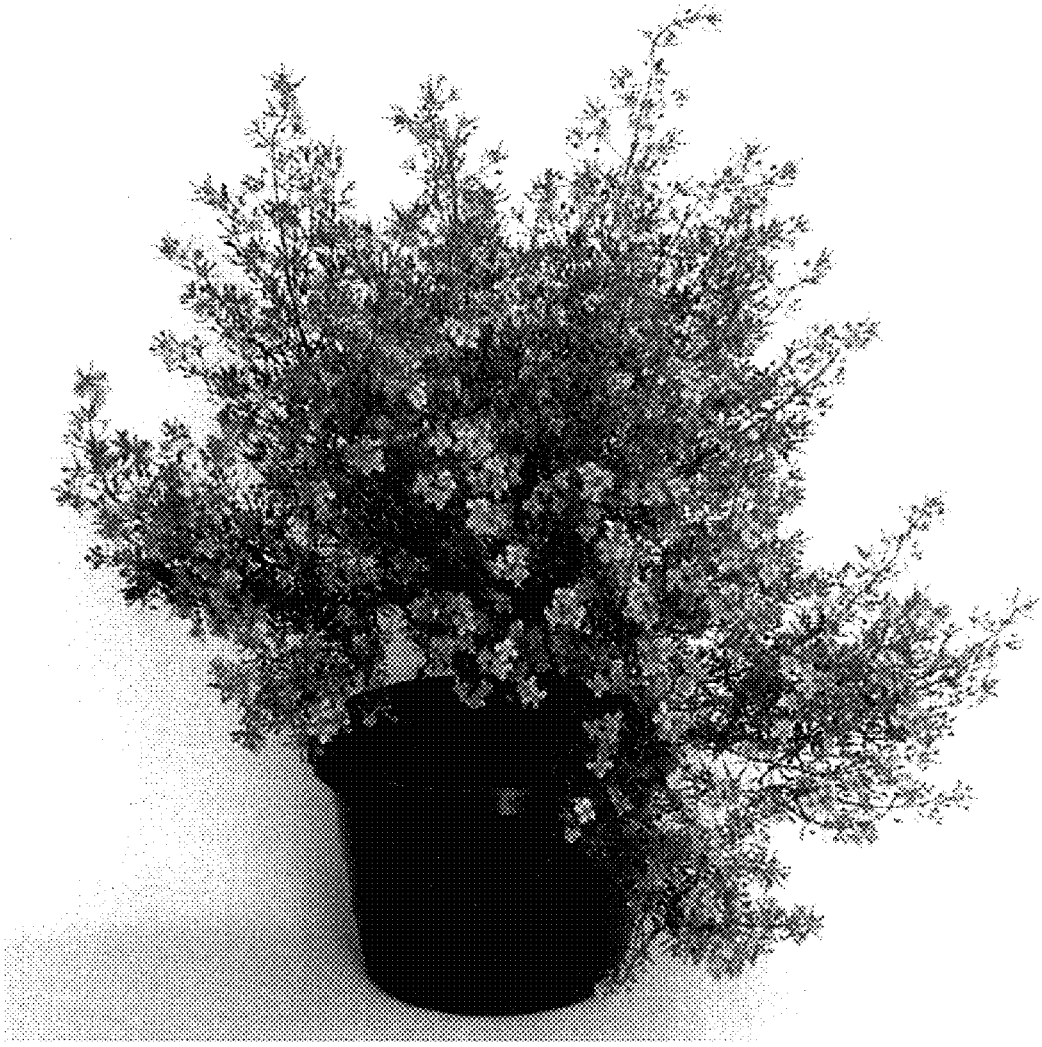

* * * * *